United States Patent [19]
Benderev

[11] Patent Number: 6,030,383
[45] Date of Patent: *Feb. 29, 2000

[54] ELECTROSURGICAL INSTRUMENT AND METHOD OF USE

[76] Inventor: Theodore V. Benderev, 26975 Magnolia Ct., Laguna Hills, Calif. 92653

[*] Notice: This patent is subject to a terminal disclaimer.

[21] Appl. No.: 09/178,849

[22] Filed: Oct. 26, 1998

Related U.S. Application Data

[63] Continuation of application No. 08/855,097, May 13, 1997, Pat. No. 5,919,189, which is a continuation-in-part of application No. 08/651,892, May 21, 1996, abandoned.

[51] Int. Cl.$^7$ .................................................. A61B 17/39
[52] U.S. Cl. ............................... 606/45; 606/41; 606/46; 606/49
[58] Field of Search ........................... 606/40–50, 37–39

[56] References Cited

U.S. PATENT DOCUMENTS

| | | | |
|---|---|---|---|
| 2,011,169 | 8/1935 | Wappler | 174/89 |
| 3,858,586 | 1/1975 | Lessen | 128/303.1 |
| 4,060,087 | 11/1977 | Hiltebrandt et al. | 128/303.15 |
| 4,116,198 | 9/1978 | Roos | 606/46 |
| 4,785,807 | 11/1988 | Blanch | 128/303.14 |
| 4,917,082 | 4/1990 | Grossi et al. | 606/42 |
| 5,160,334 | 11/1992 | Billings et al. | 606/34 |
| 5,190,541 | 3/1993 | Abele et al. | 606/46 |
| 5,196,011 | 3/1993 | Korth et al. | 606/46 |
| 5,207,675 | 5/1993 | Canday | 606/40 |
| 5,269,780 | 12/1993 | Roos | 606/42 |
| 5,318,564 | 6/1994 | Eggers | 606/47 |
| 5,403,311 | 4/1995 | Abele et al. | 606/48 |
| 5,484,435 | 1/1996 | Fleenor et al. | 606/46 |
| 5,569,244 | 10/1996 | Hahnen | 606/46 |
| 5,658,280 | 8/1997 | Issa | 606/46 |
| 5,733,283 | 3/1998 | Malis et al. | 606/48 |

OTHER PUBLICATIONS

Alexis E. Te, M.D. and Steven A. Kaplan, M.D., "Transurethral Electrovaporization of the Prostate (TVP): An Electrosurgical Advancement of the Standard TURP" in *Surgical Techniques in Urology*, vol. 8, Issue 1.

AUA Exhibit Guide: *ProSurg, The Leader in Electrosurgery for Urology* Theodore V. Benderev, M.D., Doubler Theodore V. Benderev, M.D., DeLoop T.V. Benderev, Diacut Vaportime "The Resection Electrode" of 3 pages.

*Primary Examiner*—Linda C. M. Dvorak
*Assistant Examiner*—David Ruddy
*Attorney, Agent, or Firm*—Matthew A. Newboles

[57] ABSTRACT

An electrosurgical instrument for sequentially cutting and coagulating tissue, including methodology for electrosurgical procedures incorporating principles of the inventive instrument. The instrument comprises a cutting electrode connectable to a first power source having a first power signal sufficient to cut tissue, and a coagulating electrode connectable to a second power source having a second power signal sufficient to coagulate tissue. The electrodes may be separated by an electrical insulator to maintain the electrodes in a spaced relationship such that the coagulating electrode can immediately follow the cutting electrode during movement of the instrument, thereby providing sequential yet substantially simultaneous cutting and coagulating of tissue. Methodology for performing an electrosurgical procedure in tissue includes providing the above described instrument with power delivery to the electrodes. The power signal to the cutting electrode differs from that supplied to the coagulation electrode in accord with required respective values to accomplish cutting or coagulation. The distal ends of the electrodes are introduced to tissue to be cut and moved therethrough with a single stroke to thereby effectuate tissue cutting followed by substantially simultaneous coagulation. The electrodes may be formed having differing cross-sectional configurations and may be vertically offset to maximize cutting and coagulation of tissue. An in-dwelling dispersive electrode may be utilized to concentrate electrosurgical energy at a desired tissue size.

6 Claims, 2 Drawing Sheets

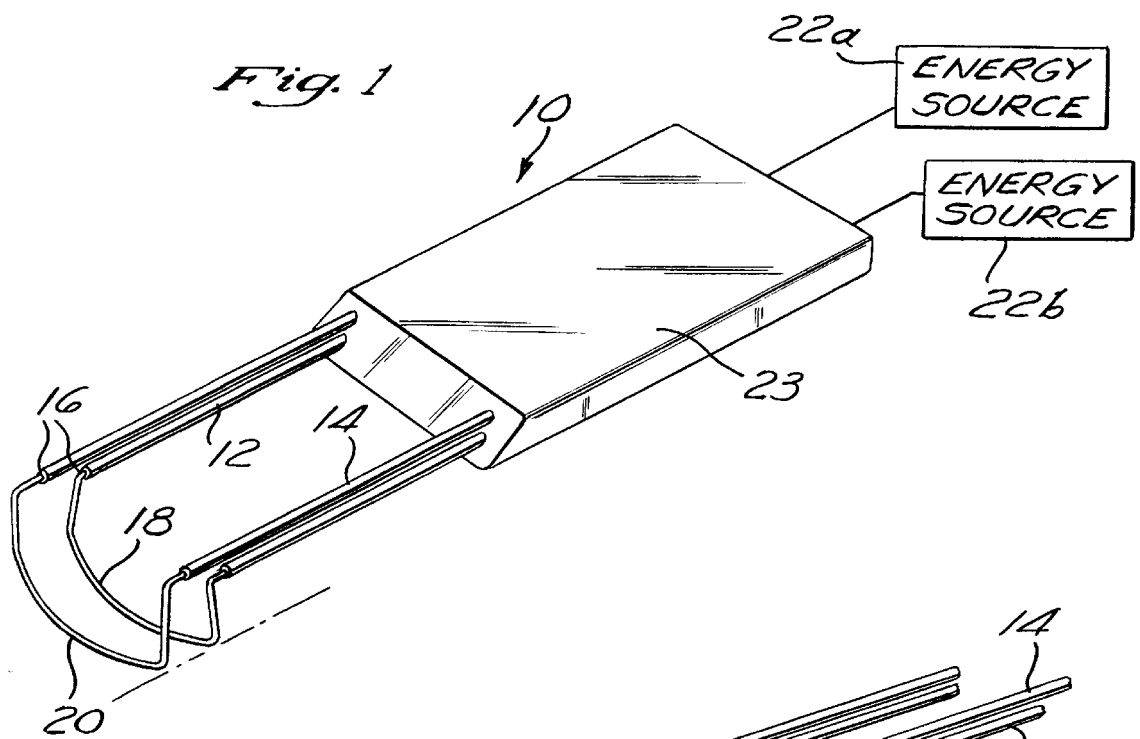
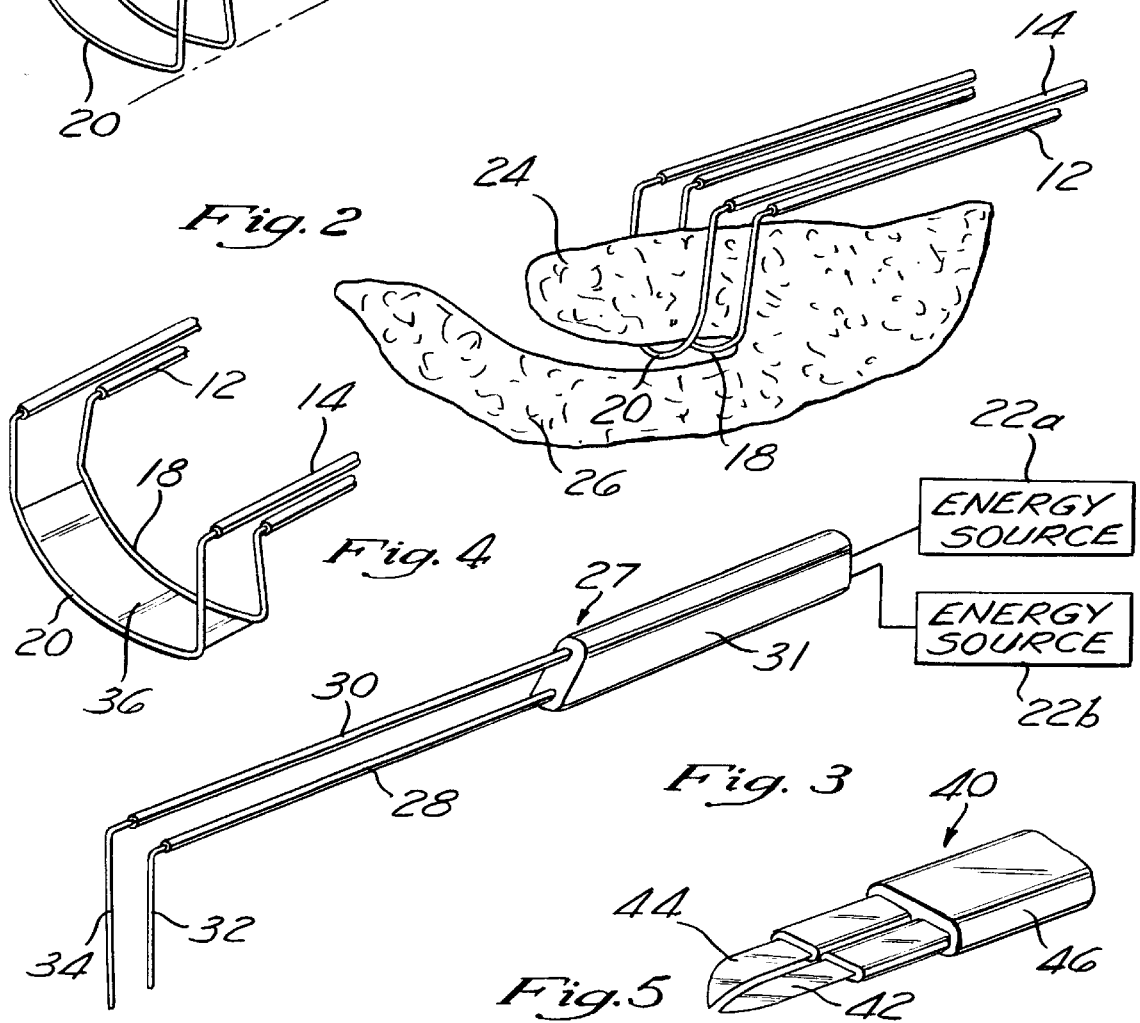

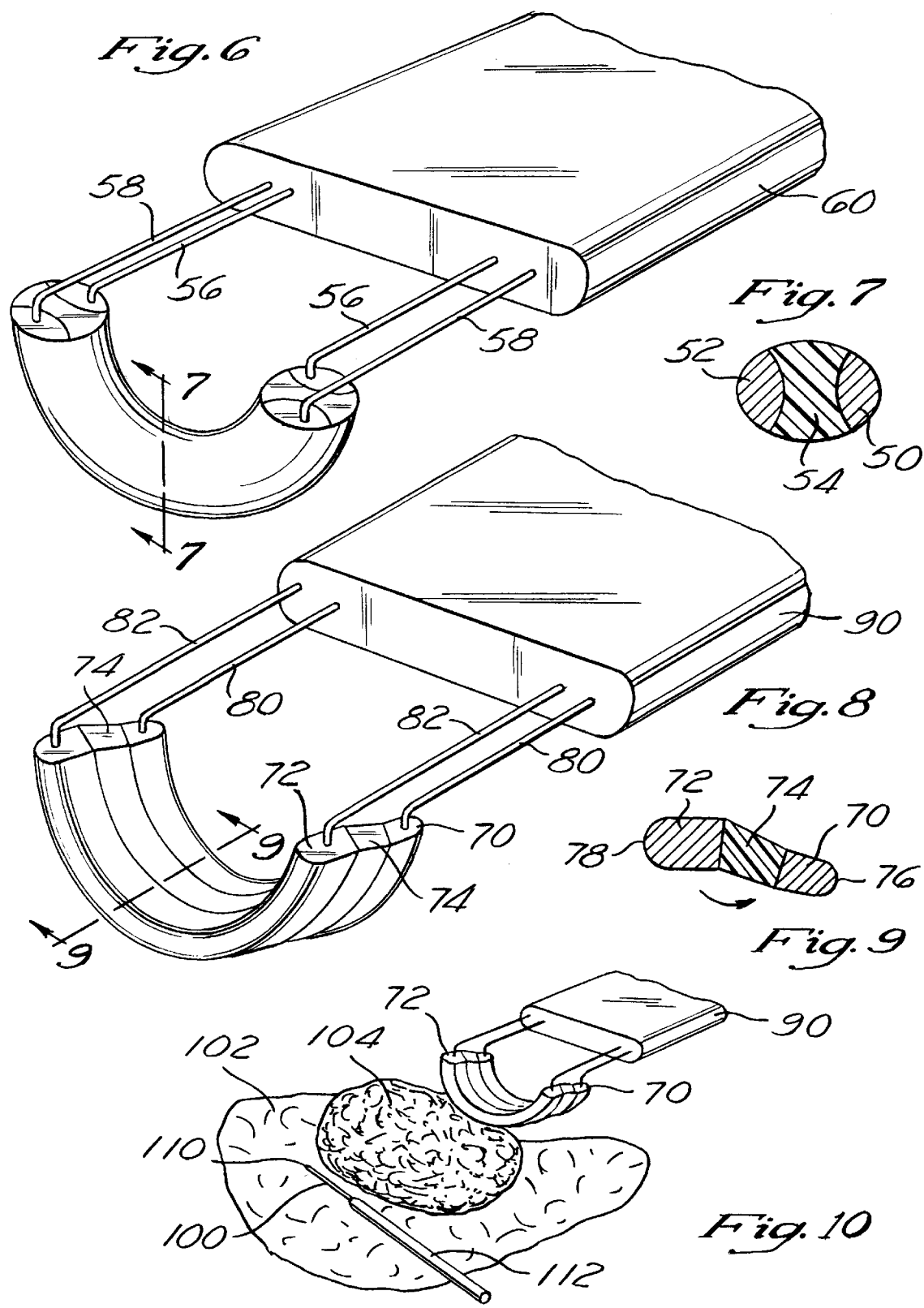

6,030,383

ELECTROSURGICAL INSTRUMENT AND METHOD OF USE

RELATED APPLICATION

The subject application is a continuation of application 08/855,097 filed May 13, 1997, now U.S. Pat. No. 5,919,189, which is a continuation-in-part application of pending U.S. Ser. No. 08/651,892, filed May 21, 1996, now abandoned in the name of Theodore V. Benderev, M.D., entitled ELECTROSURGICAL INSTRUMENT.

FIELD OF THE INVENTION

This invention relates in general to a surgical instrument, and in particular to an electrosurgical instrument that sequentially cuts or resects and coagulates tissue with one movement of the instrument through the tissue.

BACKGROUND OF THE INVENTION

The use of electrosurgical instruments for cutting and/or resecting tissue is highly effective and beneficial for accomplishing precise surgical results. In particular, a cutting electrode of a first instrument is provided with sufficient current to cut through tissue by vaporizing cellular structure in the surgical path of the electrode. Thereafter, in order to stop bleeding, a coagulation electrode of a second instrument and with a lesser magnitude of current is introduced to the surgical path to thereby coagulate transected bleeding blood vessels by desiccation, shrinkage of surrounding tissue, and/or fusion of vessel walls.

Typical prior art electrosurgical devices include a scissor-type forceps-style instrument, as described in U.S. Pat. No. 2,011,169 to Wappler; a double-loop cutting device having a proximal cutting loop connected to a live pole and a distal loop connected to a neutral pole, as described in U.S. Pat. No. 4,060,087 to Hiltebrandt et al.; a single-loop surgical snare device having two electrodes for providing bipolar cauterization, as described in U.S. Pat. No. 5,318,564 to Korth et al.; and a double loop cutting device wherein a proximal cutting loop is un-insulated and a distal insulated support loop having no power supply functions to support and guide the proximal cutting loop, as described in U.S. Pat. No. 5,318,564 to Eggers. Double loop devices having identical power amplitudes to each loop are available for singular cutting or singular coagulating activity.

Each of the above-listed devices has a single power source with a single magnitude of power. Because cutting and coagulation require different power amplitudes or signals, there is no single prior-art instrument capable of accomplishing both events from a single stroke of one instrument through affected tissue. It is therefore apparent that a need is present for such an instrument. Accordingly, and corresponding to disclosure document nos. 371167 filed Feb. 6, 1995, and Feb. 27, 1995, under the Disclosure Document Program of the United States Patent and Trademark Office, a primary object of the present invention is to provide an electrosurgical instrument capable of sequentially cutting and coagulating tissue with a single movement of the instrument through tissue.

Another object of the present invention is to provide an electrosurgical instrument with a cutting electrode having a first current magnitude appropriate for cutting tissue, and a coagulation electrode having a second current magnitude appropriate for coagulating tissue.

Another object of the present invention is to provide an electrosurgical instrument having a cutting electrode and coagulation electrode which are formed having differing cross-sectional configurations specifically adapted to allow the coagulation electrode to follow a cutting electrode and thereby promote rapid coagulation of the tissue.

Another object of the present invention is to provide an electrosurgical instrument with a cutting electrode having a first current magnitude appropriate for cutting tissue, and a coagulation electrode having a second current magnitude appropriate for coagulating tissue.

These and other objects of the present invention will become apparent throughout the description thereof which now follows.

SUMMARY OF THE INVENTION

The present invention discloses an electrosurgical instrument for sequentially cutting and coagulating tissue, and includes methodology for electrosurgical procedures incorporating principles of the inventive instrument. The instrument comprises a cutting electrode connectable to a first power source having a first power amplitude or signal sufficient to cut tissue, and a coagulating electrode connectable to a second power source having a second power amplitude sufficient to coagulate and not cut tissue. The electrodes each have respective distal ends maintained in a spaced relationship to each other such that the distal end of the coagulating electrode can immediately follow the distal end of the cutting electrode during movement of the instrument, thereby providing substantially simultaneous cutting and coagulating of affected tissue. Non-limiting paired-configurations of respective distal ends include loops, hooks, scalpel-blade shaped members, paddles, and any other configurations that beneficially accomplish resection of issue and subsequent coagulation. Dimensions and/or cross-sectional configurations of paired electrodes can be different from each other to thereby enhance as desired an electrosurgical function. Thus, for example, increasing the size of a coagulating electrode will result in greater surface area being in contact with tissue which results in greater coagulation activity.

Methodology for performing an electrosurgical procedure in tissue comprises providing the above described instrument with energy delivery to the electrodes. The power amplitude or signal to the cutting electrode is preferably greater than that supplied to the coagulation electrode in accord with required respective amplitudes to accomplish cutting and coagulation. The charged instrument is then introduced to the tissue to be cut and moved therethrough with a single stroke that effectuates tissue cutting and coagulation.

BRIEF DESCRIPTION OF THE DRAWINGS

An illustrative and presently preferred embodiment of the invention is shown in the accompanying drawings in which:

FIG. 1 is a perspective view of an electrosurgical instrument having uniformly-shaped semi-circular loop electrodes for tissue resection;

FIG. 2 is a perspective view of the instrument of FIG. 1 in tissue;

FIG. 3 is a perspective view of a second embodiment of an electrosurgical instrument having hook-shaped electrodes;

FIG. 4 is a perspective view of a third embodiment of double loop construction similar to FIG. 1 except with a separator membrane;

FIG. 5 is a perspective view of a forward portion of a fourth embodiment of an electrosurgical instrument having generally scalpel-blade shaped electrodes;

FIG. 6 is a perspective view of a fifth embodiment of an electrosurgical instrument wherein the cutting electrode and coagulation electrode are separated by an electrical insulator and the electrodes and electrical insulator are maintained in a contiguous, generally integral configuration so as to promote ease and manipulation of the instrument through tissue;

FIG. 7 is a cross-sectional view taken about lines 7—7 of FIG. 6;

FIG. 8 is a perspective view of a sixth embodiment of an electrosurgical instrument wherein the cutting electrode and coagulation electrode are specifically formed having differing cross-sectional configurations to allow the coagulation electrode to follow and contact the tissue during resection;

FIG. 9 is a cross-sectional view taken about lines 9—9 of FIG. 8; and

FIG. 10 is a perspective view of the electrosurgical instrument of FIG. 8 in tissue being utilized with a dispersive electrode positioned in dwelling within the patient adjacent to or residing within the surgical site.

DETAILED DESCRIPTION OF THE PREFERRED EMBODIMENT

Referring to FIG. 1, an electrosurgical instrument 10 having a cutting electrode 12 and a coagulation electrode 14 is shown. Each electrode 12, 14 is an electrically conductive metal wire, preferably formed of stainless steel, having electrical insulation 16 along its length except for noninsulated distal uniformly-shaped semi-circular loops 18, 20 employed in surgical procedures. The non-insulated loops 18, 20 are preferably positioned or spaced from one another to prevent any electrical arcing within the tissue. Should the non-insulated loops 18, 20 arc while in tissue, the loops 18, 20 may be operative to provide only coagulation, thereby safely preventing any cutting action without subsequent coagulation action. The electrodes 12, 14 are connectable through a non-conducting handle member 23 to preferably two separate standard electrical energy sources 22a, 22b capable of delivering different selectable power or signal values simultaneously to the two electrodes 12, 14. As illustrated herein, the loop 18 of the cutting electrode 12 is positioned proximally from the loop 20 of the coagulation electrode 14, but such designation is determined solely by the amplitude of power being delivered to the respective electrodes 12, 14 since illustrated electrode-construction is identical. Thus, while single-direction movement only is typical, the instrument 10 can be moved in a forward or rearward direction by simply reversing current magnitude delivered to the electrodes 12, 14. Movement, of course, must be such that the loop of the coagulation electrode follows the loop of the cutting electrode in substantially the same pathway. It is to be understood, however, that the electrodes can differ from each other, with, for example, a distal coagulating electrode loop being broader to thereby contact tissue for a longer period of time. Additionally, the distal electrode can be constructed of spring steel. This construction assures that, after the proximal cutting electrode makes site contact, the distal coagulating electrode also follows with substantially the same site contact to thereby effectuate coagulation immediately after cutting.

Referring to FIG. 2, the loop 18 of the cutting electrode 12 is shown performing a tissue resection of portion 24 from a tissue base 26 by moving the instrument 10 in the direction of the arrow. Thus, the loop 18 of the cutting electrode 12 first cuts cells originally situated between the tissue portion 24 and tissue base 26, and the loop 20 of the coagulation electrode 14 sequentially substantially immediately thereafter coagulates the transected blood vessels in the tissue base 26 to thereby cause coagulation. The power amplitude or signal delivered to the cutting electrode 12 is preferably between about 150 and about 300 watts, while power amplitude delivered to the coagulation electrode 14 is preferably between about 80 and about 140 watts.

FIG. 3 illustrates a second embodiment of an electrosurgical instrument 27 wherein a cutting electrode 28 and coagulation electrode 30 are hook-shaped for use where such a configuration is beneficial. As in the embodiment shown in FIG. 1, each electrode 28, 30 is constructed of an electrically conductive metal wire having electrical insulation 16 along its length except for the non-insulated distal hooks 32, 34 employed in surgical procedures. As with the non-insulated loops 18, 20 of the instrument 10, should the non-insulated hooks 32, 34 arc while in tissue, the hooks 32, 34 may be operative to only provide coagulation, thereby safely preventing any cutting action without subsequent coagulation action. The electrodes 28, 30 are connectable through a non-conductive handle member 31 to two separate standard electrical energy sources 22a, 22b capable of delivering different selectable power values simultaneously to the two electrodes 28, 30. As illustrated and as explained above in relation to the loops 18, 20 of the electrodes 12, 14, the hook 32 of the cutting electrode 28 is positioned proximally from the hook 34 of the coagulation electrode 30, but such designation is determined solely by the magnitude of current being delivered to the respective electrodes 12, 14 since electrode construction is identical. Thus, and while single-direction movement only is typical, the instrument 27 can be moved in a forward or rearward direction by simply reversing current magnitude delivered to the electrodes 28, 30. Movement, of course, must be such that the hook of the coagulation electrode follows the hook of the cutting electrode in substantially the same pathway. It is to be understood, however, that the electrodes can differ from each other, with, for example, a distal coagulating electrode hook being broader to thereby contact tissue for a longer period of time. Additionally, the distal electrode can be constructed of spring steel so that its tissue contact path is substantially the same as that of the proximal cutting electrode and coagulation immediately follows cutting. Power amplitudes for cutting and for coagulation are substantially similar to those recited above for the instrument 10. As in all embodiments, the patient functions as ground, or a third pole at the site functions as ground with use of this embodiment.

As earlier noted, a double-loop cutting portion embodiment shown in FIG. 4 is similar to the instrument 10 of FIG. 1, except that a flexible, semi-rigid or rigid membrane 36 formed of an electrically insulated material is disposed between the electrode loops 18, 20 to thereby avoid tissue becoming lodged between these loops and to prevent arcing.

FIG. 5 illustrates a two-element cutting portion embodiment 40 comprising two tandem members 42, 44 wherein the first member 42 is shorter and functions as a cutting electrode, while the second member 44 is longer to thereby follow the first member 42 and functions as a coagulating electrode. The two members together resemble a single scalpel blade split and spaced along a central vertical axis. While the members 42, 44 are scalpel-blade shaped, they do not need to be sharp. Thus, for example, the cutting member can be sharp or dull, while the coagulating member is dull. The members 42, 44 project from an insulated handle member 46 in substantially the same manner as the electrodes of the embodiment of FIG. 1, and each is connected to a separate power source (not shown) as in the embodiments of FIGS. 1 and 3. The members 42 and 44 are spaced from one another to prevent arcing and/or may be provided with electrical insulation to prevent arcing between themselves in tissue. Power amplitude to the cutting first member 42 is greater than that to the coagulating second member 44, with respective values being substantially the same as defined for the embodiment of FIG. 1. The patient functions as ground, or a third pole or dispersive electrode (not shown) at the site functions as ground with use of this embodiment. As with the non-insulated loops 18, 20 of the instrument 10, should the non-insulated members 42, 44 arc while in tissue, members 42, 44 may be operative to provide coagulation, thereby safely preventing any cutting action without subsequent coagulation action.

Use of any of the embodiments according to the principles of the present invention is accomplished as described above in relation to the illustration of FIG. 2. Thus, a surgeon connects an embodiment to respective power sources such that the cutting electrode thereof has sufficient power signal to cut tissue while the coagulating electrode thereof has sufficient power to coagulate and not cut tissue. Thereafter, the electrodes are introduced to and drawn through tissue to be cut such that the coagulating electrode immediately follows the cutting electrode.

Referring to FIG. 6, an additional embodiment of the electrosurgical instrument of the present invention is depicted wherein the cutting electrode and coagulation electrode are separated by an electrical insulator and formed in a contiguous orientation to approximate the feel of a conventional prior art single wire loop electrosurgical instrument. More particularly, as shown in FIG. 6, the cutting electrode 50 and coagulation electrode 52 are both formed in an arcuate wire loop configuration and are separated by an electrical insulator 54. As best shown in FIG. 7, the electrical insulator 54 is formed having an hourglass-like configuration and is permanently affixed to both cutting electrode 50 and coagulation electrode 52. Each of the electrodes 50 and 52 are electrically connected by insulated conductors 56 and 58 which extend through the hand piece or handle 60 and are each connected to a respective pair of power sources 22a and 22b (shown in FIG. 1). As in the other embodiments of the present invention, actuation of the power sources 22a and 22b cause differing electrosurgical power signals to be supplied to the cutting electrode 50 and coagulation electrode 52.

It will be recognized that in the embodiment of FIG. 6, the electrosurgical instrument closely approximates the configuration and tactile feel of a conventional single-loop electrosurgical instrument as that currently utilized in the art. As such, the surgeon may easily manipulate the electrosurgical instrument in a manner substantially identical to that previously utilized while performing a cutting as well as coagulation function in a single movement through tissue. Further, if desired, the surgeon may pivot or rotate the electrosurgical instrument after cutting and subsequently move the instrument backward over the cut tissue with only the coagulation electrode contacting the tissue to insure that desired coagulation is being achieved upon the tissue.

Referring to FIG. 8, an additional embodiment of the electrosurgical instrument of the present invention is disclosed which is similar to the embodiment of FIG. 6 but includes differing shaped cutting and coagulation electrodes specifically adapted to promote cutting and coagulation functions. As shown in FIG. 8, in this embodiment of the present invention, the cutting electrode 70 and coagulation electrode 72 are additionally preferably formed in an arcuate wire loop configuration separated by an electrical insulator 74. However, as opposed to the embodiment shown in FIG. 6, in this embodiment, the cutting electrode 70 and coagulation electrode 72 are formed having differing cross-sectional configurations specifically adapted to promote cutting and coagulation of tissue.

Referring to FIG. 9, the differing cross-sectional configurations of the electrode 70 and 72 are depicted. As shown, the cutting electrode 70 preferably is formed having a smaller cross-sectional configuration then the coagulation electrode 72. Additionally, the leading edge of the cutting electrode 70 is preferably formed having a smaller radius 76 then the trailing edge radius 78 of the coagulation electrode. As in the previous embodiments, insulated conductors 80 and 82 serve to electrically interface the electrodes 70 and 72 to a pair of energy or power sources 22a and 22b (shown in FIG. 1) through the handle member 90.

As depicted in FIG. 9, it will be noted that the cutting electrode 70 and coagulation electrode 72 are preferably vertically offset from one another which, in combination with their differing cross-sectional configurations, serves to promote a proper following or tracking of the coagulation electrode 72 relative the cutting electrode 70 through tissue (i.e., the particular configuration and offset spacing of the electrodes 70 and 72 promotes proper contact of the coagulation electrode 72 with the tissue after cutting). Further, due to the surface area of the coagulation electrode 72 be greater than the surface area of the cutting electrode 70, the tissue is contacted for a greater time duration to promote proper coagulation. Additionally, by pivoting or rotating the electrosurgical instrument during tissue resection in a counter-clockwise direction as depicted by the arrow in FIG. 9, it will be recognized that the coagulation electrode 72 will be pressed downwardly against the cut tissue to promote coagulation.

Referring to FIG. 10, the electrosurgical instrument of FIG. 8 is depicted in use in a tissue cutting application. Although the electrosurgical instrument can be utilized with a conventional dispersive electrode(s) (not shown) which is applied to the patient's body at a site away from the surgical field, the present invention additionally contemplates the use of an in-dwelling dispersive electrode 100 which may be inserted into the patient's body 102 to reside within or adjacent the surgical site 104. In the preferred embodiment, the in-dwelling electrode 100 comprises one or more hypodermic needles or stylets having an electrically conductive distal end 110 and an electrically insulated sleeve 112. The proximal end of the hypodermic needle 100 may be connected via conventional conductors (not shown) to the electrosurgical generator or power source 22a and 22b (shown in FIG. 1). Further, it is contemplated that a electrically conductive fluid, such as a hypertonic saline solution, may be injected through the needle 100 to reside in the tissue surrounding the operative site. In use, when the electrosurgical procedure is initiated by applying power to the cutting electrode 70 and coagulation electrode 72, electrosurgical power is dispersed from the electrosurgical instrument through the surgical site 104 into the saline solution and into in-dwelling dispersive electrode 100. Due to the close proximity of the in-dwelling dispersive electrode 100 to the surgical site 104, electrosurgery results from the concentration of electrical energy in the surgical site 104 such that the local tissue is cut and/or coagulated. Further, due to the saline solution forming an enlarged and greater electrically conductive area or volume within the patient, cutting or burning of tissue adjacent to the operative site and proximal the needle 100 is minimized, and a preferential electrical path from the electrodes 70 and 72 to the dispersive electrode needle 100 is facilitated.

Although the embodiments shown herein illustrate various constructions for the cutting and coagulating elements, it is to be understood that the principle of delivering different power amplitudes to elements of electrosurgical instruments of any appropriate configuration in accord with the respective function (cutting or coagulating) of those elements is included within the scope of the present invention. Further, although for purposes of illustration, the energy or power sources 22a and 22b have been described as separate discrete power generators, those skilled in the art will recognize that the same may be embodied as a single source having dual power outputs. Therefore, while illustrative and presently preferred embodiments of the invention have been described in detail herein, it is to be understood that the inventive concepts may be otherwise variously embodied and employed and that the appended claims are intended to be construed to include such variations except insofar as limited by the prior art.

What is claimed is:

1. An electrosurgical instrument for sequentially cutting and coagulating tissue, the instrument comprising:
   a) a cutting electrode loop connectible to a first power source capable of delivering a first power signal sufficient to cut tissue;
   b) a coagulation electrode loop connectible to a second power source capable of delivering a second power signal sufficient to coagulate tissue; and
   c) a substantially smooth-walled electrical insulator extending from said cutting electrode loop and toward said coagulating electrode loop such that in use, said electrical insulator forms a smooth bridge between said electrodes and maintains said electrodes in spaced relationship to each other such that the coagulating electrode can immediately follow the cutting electrode during a single movement of the instrument through tissue.

2. An electrosurgical instrument for sequentially cutting and coagulating tissue, the instrument comprising:
   a) a cutting electrode loop connectible to a first power source capable of delivering a first power signal sufficient to cut tissue;
   b) a coagulation electrode loop connectible to a second power source capable of delivering a second power signal sufficient to coagulate tissue; and
   c) a substantially smooth-walled electrical insulator extending from said coagulating electrode loop and toward said cutting electrode loop such that in use, said electrical insulator forms a smooth bridge between said electrodes and maintains said electrodes in spaced relationship to each other such that the cutting electrode can immediately precede the coagulating electrode during a single movement of the instrument through tissue.

3. An electrosurgical instrument for sequentially cutting and coagulating tissue, the instrument comprising:
   a) a cutting electrode loop connectible to a first power source capable of delivering a first power signal sufficient to cut tissue;
   b) a coagulation electrode loop connectible to a second power source capable of delivering a second power signal sufficient to coagulate tissue;
   c) a first substantially smooth-walled electrical insulator extending from said cutting electrode loop; and
   d) a second substantially smooth-walled electrical insulator extending from said coagulating electrode loop, said second smooth-walled electrical insulator being designed to mate and abut with said first smooth-walled electrical insulator such that in use, said electrical insulators provide a smooth bridge between said electrodes and maintain said electrodes in spaced relationship to each other such that the coagulating electrode can immediately follow the cutting during a single movement of the instrument through tissue.

4. A method for performing an electrosurgical procedure in tissue, the method comprising:
   a) providing an electrical surgical instrument comprising a cutting electrode loop connectible to a first power source capable of delivering a first power signal sufficient to cut tissue, a coagulating electrode connectible to a second power source capable of delivering a second power signal sufficient to coagulate tissue, and a substantially smooth-walled electrical insulator extending from said cutting electrode loop toward said coagulating electrode loop to maintain said electrodes in spaced relationship to each other during such method and to provide a smooth bridge between said electrode loops such that the coagulating electrode can immediately follow the cutting electrode during a single movement of the instrument through tissue.

5. A method for performing an electrosurgical procedure in tissue, the method comprising:
   a) providing an electrical surgical instrument comprising a cutting electrode loop connectible to a first power source capable of delivering a first power signal sufficient to cut tissue, a coagulating electrode connectible to a second power source capable of delivering a second power signal sufficient to coagulate tissue, and a substantially smooth-walled electrical insulator extending from said coagulating electrode loop toward said cutting electrode loop to maintain said electrodes in spaced relationship to each other during such method and to provide a smooth bridge between said electrode loops such that the coagulating electrode can immediately follow the cutting electrode during a single movement of the instrument through tissue.

6. A method for performing an electrosurgical procedure in tissue, the method comprising:
   a) providing an electrical surgical instrument comprising a cutting electrode loop connectible to a first power source capable of delivering a first power signal sufficient to cut tissue, a coagulating electrode connectible to a second power source capable of delivering a second power signal sufficient to coagulate tissue, a first substantially smooth-walled electrical insulator extending from said cutting electrode loop, a second substantially smooth-walled electrical insulator extending from said coagulating electrode loop toward said first electrical insulator to maintain said electrodes in a space relationship to each other during such method and to provide a smooth bridge between said electrode loops such that the coagulating electrode can immediately follow the cutting electrode during a single movement of the instrument through tissue.

* * * * *